(12) United States Patent
Witt et al.

(10) Patent No.: US 9,081,044 B2
(45) Date of Patent: Jul. 14, 2015

(54) DETECTION CELL WITH CONTROLLED POWER DISSIPATION

(75) Inventors: Klaus Witt, Keltern (DE); Bohuslav Gas, Jilove u Prahy (CZ)

(73) Assignee: Agilent Technologies, Inc., Santa Clara, CA (US)

( * ) Notice: Subject to any disclaimer, the term of this patent is extended or adjusted under 35 U.S.C. 154(b) by 1580 days.

(21) Appl. No.: 11/726,014

(22) Filed: Mar. 20, 2007

(65) Prior Publication Data

US 2007/0190660 A1 Aug. 16, 2007
US 2013/0267033 A9 Oct. 10, 2013

Related U.S. Application Data

(63) Continuation of application No. PCT/EP2004/052278, filed on Sep. 23, 2004.

(51) Int. Cl.
*G01R 27/26* (2006.01)
*G01F 23/26* (2006.01)
*G01N 27/447* (2006.01)
*G01N 30/64* (2006.01)

(52) U.S. Cl.
CPC ........ *G01R 27/2623* (2013.01); *G01N 27/4473* (2013.01); *G01N 2030/645* (2013.01)

(58) Field of Classification Search
USPC ........ 73/304 C; 324/663, 665, 667, 669, 691; 422/42.02; 47/20.1–32.3
See application file for complete search history.

(56) References Cited

U.S. PATENT DOCUMENTS

| 3,965,414 A | 6/1976 | Teass, Jr. |
| 5,087,870 A | 2/1992 | Salesky et al. |
| 5,210,500 A | 5/1993 | Pingel et al. |
| 5,248,426 A * | 9/1993 | Stillian et al. ................. 210/635 |
| 2003/0039299 A1* | 2/2003 | Horovitz et al. ............... 374/141 |
| 2003/0222664 A1 | 12/2003 | Goor et al. |

FOREIGN PATENT DOCUMENTS

CS    270 085    8/1989

OTHER PUBLICATIONS

International Search Report completed Mar. 30, 2005 Written Opinion completed Apr. 15, 2005.

* cited by examiner

*Primary Examiner* — In Suk Bullock
*Assistant Examiner* — Robert Eom

(57) ABSTRACT

A voltage control circuitry for a detection cell is described, where the detection cell is adapted for determining an electrical property of a sample in a detection cell volume of the detection cell. The voltage control circuitry comprises a power supply adapted for providing a voltage to the detection cell, and a power evaluation unit adapted for determining an actual power dissipation in the detection cell volume. The voltage control circuitry further comprises a control unit adapted for comparing the actual power dissipation with a desired power dissipation, and for regulating the power supply's voltage in a way that the actual power dissipation is driven towards the desired power dissipation.

21 Claims, 2 Drawing Sheets

DETECTION CELL WITH CONTROLLED POWER DISSIPATION

This application is the National Stage of International Application No. PCT/EP2004/052278, filed on 23 Sep. 2004, which designated the United States of America, and which international application was published as WO Publication No. WO 2006/032304 and which is incorporated by reference in its entirety.

BACKGROUND ART

The present invention relates to a voltage control circuitry for a detection cell, to a current control circuitry for a detection cell, and to a separation system. The invention further relates to a method for determining an electrical property of a sample.

A detection cell, like e.g. a contactless conductivity detection (CCD) cell, is adapted for analyzing an electrical property of a fluid sample. A detection cell might e.g. be part of a flow path, in order to detect various compounds of a fluid sample. When designing a detection cell, the aim is to arrive at a good resolution of the obtained spectra or record, and to reduce the limit of detection (LOD), which is a measure of the minimum concentration required for detecting a certain compound.

For detecting a respective electrical property, a voltage is applied across the detection cell volume. In prior art solutions, it has been attempted to improve the measurement accuracy by keeping the applied voltage as constant as possible. Or, if that is difficult, it's variance is compensated for the read-out. For example, the Czech patent CS Certification AO 270085 dealing with "auto-calibration principle" was registered in 1991. The voltage of the generator is evaluated and serves as a reference voltage to correct the read-out.

DISCLOSURE OF THE INVENTION

It is an object of the invention to further improve the quality of the measurements of a detection cell. The object is solved by the independent claim(s). Preferred embodiments are shown by the dependent claim(s).

According to embodiments of the present invention, a voltage control circuitry for a detection cell is provided, whereby the detection cell is adapted for determining an electrical property of a sample in a detection cell volume of the detection cell. The voltage control circuitry comprises a power supply adapted for providing a voltage to the detection cell, and a power evaluation unit adapted for determining an actual power dissipation in the detection cell volume. The voltage control circuitry further comprises a control unit adapted for comparing the actual power dissipation with a desired power dissipation, and for regulating the power supply's voltage in a way that the actual power dissipation is driven towards the desired power dissipation.

In this solution, the voltage applied across the detection cell volume is no longer kept constant. Instead, the voltage may be varied within a predefined voltage range. The control unit is adapted for adjusting the voltage such that the power dissipated in the detection cell volume is approximately kept constant. As the real part of the power dissipation is proportional to the heat dissipation within the detection cell volume, the heat dissipation in the detection cell is kept constant as well.

In detection cells of the prior art, it has always been tried to keep the voltage applied to the detection cell as stable as possible. Another electrical property, like e.g. the current, can then be used for determining the conductivity of the fluid sample, or any other electrical property of the fluid sample. However, when a sample band of high conductivity is conveyed through the detection cell, a significant increase of the current is observed, and the power dissipation within the detection cell volume goes up as well. Hence, the conductivity band experiences an energy pulse, and because the detection cell volume is rather small (in the order of 10 nl), the fluid contained in the detection cell is heated up and might even start boiling. Even if the constant voltage is chosen such that boiling is prevented, the temperature disturbance will cause artifacts, like e.g. baseline variations, and the quality of the obtained spectra or record will be deteriorated. The voltage across the detection cell therefore has to be chosen such that even in case of high-conductivity bands, the temperature disturbances are kept small. As a consequence, a rather weak signal will be obtained when a sample band of low conductivity moves by. For low-conductivity sample bands, the signal-to-noise ratio of the obtained signal is not at its optimum.

By controlling the applied power in a way that the Joule heating is stabilized, much better results are obtained. In case a high-conductivity sample band is conveyed through the detection cell volume, the control unit reduces the applied voltage, and heat dissipation is stabilized. Disturbances due to a sudden rise of temperature do not occur any more. In case a low-conductivity sample band moves by, the applied voltage is increased, and the power dissipation is kept at its predefined value. By tuning up the voltage, a strong signal having a good signal-to-noise ratio is obtained. Furthermore, the limit of detection (LOD) for a compound can be reduced, which means that even small concentrations of the compound can be detected. Due to the dynamic adjustment of the applied voltage, the detection cell behaves like a "magnifying glass" when detecting low-conductivity sample compounds.

Another aspect is that electrical properties of a liquid with a known concentration of ions are strongly dependent on temperature. A change in temperature gives rise to a corresponding change of the medium's viscosity, at a rate of approximately 2% per degree Celsius. As the mobility of the ions depends on the medium's viscosity, the mobility is changed as well, which in turn affects the electrical properties of the sample compound, like e.g. the sample compound's conductivity. For this reason, electrical properties of different sample compounds should not be measured at different temperatures. It is therefore advantageous to control the heat dissipation within the detection cell in a way that a stable temperature profile is accomplished.

In a preferred embodiment, the control unit is adapted for determining the variance between the actual power dissipation and a set value indicating a desired power dissipation. Then, the voltage across the detection cell is adjusted such the variance is reduced. For example, if the actual power dissipation is higher than the desired power dissipation, the applied voltage will have to be reduced. In contrast, if the actual power dissipation is below the predefined set value, the voltage across the detection cell will be increased.

According to a preferred embodiment, the applied voltage is an AC voltage. In another preferred embodiment, an AC voltage with a frequency between 10 kHz and 1 GHz is provided to the detection cell.

In a preferred embodiment, the electrical property is at least one of: conductivity, complex conductivity, impedance, resistance, reactance, relative permittivity, and dielectric dispersion. Detecting one or more of the above-mentioned electrical properties allows to detect and characterize a particular compound.

In a further preferred embodiment, a current through the detection cell is determined. For this purpose, the voltage control circuitry might e.g. comprise a current determination unit. When both the voltage across the detection cell and the current through the detection cell are known, one or more of the above-mentioned electrical properties of the fluid sample can be derived there from.

Furthermore, according to another preferred embodiment, the applied voltage and the current can be used for determining the actual power dissipation in the detection cell volume. The power evaluation unit might comprise a multiplier adapted for multiplying the voltage and the current, and for forwarding the obtained power to the control unit.

In a preferred embodiment, the multiplier is adapted for separately determining the real part of the product of voltage and current, because the real part of the product corresponds to Joule heating, whereas the imaginary part of the product does not contribute to heat dissipation. By performing a phase-sensitive evaluation of the product, a more accurate control of Joule heating is accomplished.

In yet another preferred embodiment, the power supply is implemented as a voltage-controlled power supply adapted for receiving a voltage control signal from the control unit, whereby the output voltage of the power supply is varied in dependence on the magnitude of the voltage control signal.

According to a preferred embodiment, the control unit is adapted for adjusting the voltage provided by the power supply at a rate between 100 Hz and 100 kHz. On the one hand, the control unit's rate of operation should be high enough to allow for a quick reaction to any changes of the sample's electrical properties. On the other hand, the rate of operation should be smaller than the frequency of the AC voltage provided by the power supply.

In a further preferred embodiment, the voltage control circuitry comprises a divider unit adapted for receiving signals indicating the applied voltage as well as the current through the detection cell, and for determining a quotient of the current and the voltage. This quotient corresponds to the sample's conductivity. Furthermore, this quotient can be used for deriving any other electrical property of interest.

According to another preferred embodiment, the divider unit is adapted for separately determining at least one of the real and the imaginary part of the quotient of the current and the voltage. A phase-sensitive evaluation of the quotient allows to derive a wide variety of electrical properties of the sample. For example, the (complex) impedance can be obtained as the inverse of the complex conductivity. Then, the sample's resistance and the sample's reactance can be obtained as the real and the imaginary part of the impedance, respectively.

In an alternative embodiment, a current control circuitry for a detection cell is provided. The detection cell is adapted for determining an electrical property of a sample in a detection cell volume of the detection cell. The current control circuitry comprises a power supply adapted for providing a current to the detection cell, a power evaluation unit adapted for determining an actual power dissipation in the detection cell volume, and a control unit. The control unit is adapted for comparing the actual power dissipation with a desired power dissipation, and for regulating the power supply's current in a way that the actual power dissipation is driven towards the desired power dissipation.

In this embodiment, the power supply is adapted for providing a current to the detection cell, whereby the magnitude of the current is regulated in a way that the power dissipation is driven towards a desired value. If the power dissipation is too high, the current through the detection cell will be reduced, and if the power dissipation is too small, the current will be increased. Hence, the heat dissipation within the detection cell is stabilized. Furthermore, the detection cell's sensitivity is improved.

Preferably, the current applied to the detection cell is an AC current, further preferably an AC current with a frequency between 10 kHz and 1 GHz.

In a preferred embodiment, the current control circuitry comprises a multiplier adapted for multiplying the current with the voltage across the detection cell. As a result, the power dissipation is obtained. Further preferably, the current control circuitry comprises a divider adapted for dividing the current and the voltage across the detection cell, in order to derive an electrical property of interest.

Embodiments of the invention further relate to a detection cell adapted for determining an electrical property of a sample in a detection cell volume of the detection cell. The detection cell comprises a transmitter electrode adapted for capacitively coupling a current to the detection cell volume, and a receiver electrode adapted for receiving the current that has been coupled to the detection cell volume. Furthermore, the detection cell either comprises voltage control circuitry as described above, or current control circuitry as described above.

In a preferred embodiment, the detection cell is implemented as a contactless conductivity detection (CCD) cell.

In one preferred embodiment, the electrodes are arranged in a radial geometry. The radial geometry allows for the smallest possible detection cell volume, which is a key requirement for obtaining sharp transitions between different sample bands.

In an alternatively preferred embodiment, the electrodes are axially separated. Especially at high voltages and large currents, crosstalk between the electrodes might impair the obtained spectra. Preferably, the axial separation between the electrodes is chosen such that disturbances due to crosstalk are kept small.

According the yet another preferred embodiment, the detection cell is implemented on a microfluidic chip device. The volume of a detection cell on a microfluidic chip device might be as small as 10 nl. Such a small volume of fluid sample can be heated up quickly. Embodiments of the present invention allow for a precise control of the heat dissipation.

Embodiments of the present invention further relate to a separation system comprising a separation flow path adapted for separating sample compounds of a given sample, and a detection cell as described above. In a further preferred embodiment, the separation system is at least one of: an electrophoresis system, a liquid chromatography system, an electro-chromatography system, and an isotachophoresis system.

The invention can be partly or entirely embodied or supported by one or more suitable software programs, which can be stored on or otherwise provided by any kind of data carrier, and which might be executed in or by any suitable data processing unit.

BRIEF DESCRIPTION OF DRAWINGS

Other objects and many of the attendant advantages of embodiments of the present invention will be readily appreciated and become better understood by reference to the following more detailed description of preferred embodiments in connection with the accompanied drawing(s). Features that are substantially or functionally equal or similar will be referred to with the same reference sign(s).

In FIG. 1, a first embodiment of the invention is shown. An electrical property of a fluid sample contained in a detection cell volume 2 is determined by a detection cell 1. For example, the detection cell 1 might be adapted for determining the conductivity of sample bands conveyed through the detection cell volume 2. The sample compounds might have been separated in a preceding separation flow path. The detection cell 1 is implemented as a contactless conductivity detection (CCD) cell. The detection cell 1 comprises a transmitter electrode 3 and a receiver electrode 4 arranged in a radial geometry. The radial approach features the smallest possible detection cell volume. The transmitter electrode 3 is connected with a HF power supply 5, which provides a HF voltage 6 to the transmitter electrode 3. The HF power supply 5 is a voltage controlled power supply, which means that the magnitude of the HF voltage 6 at the power supply's output is varied in accordance with the magnitude of a DC control voltage 7 at the power supply's input. The HF voltage 6 is provided, as a first input, to a multiplier unit 8 and to a divider unit 9.

Figure 1:
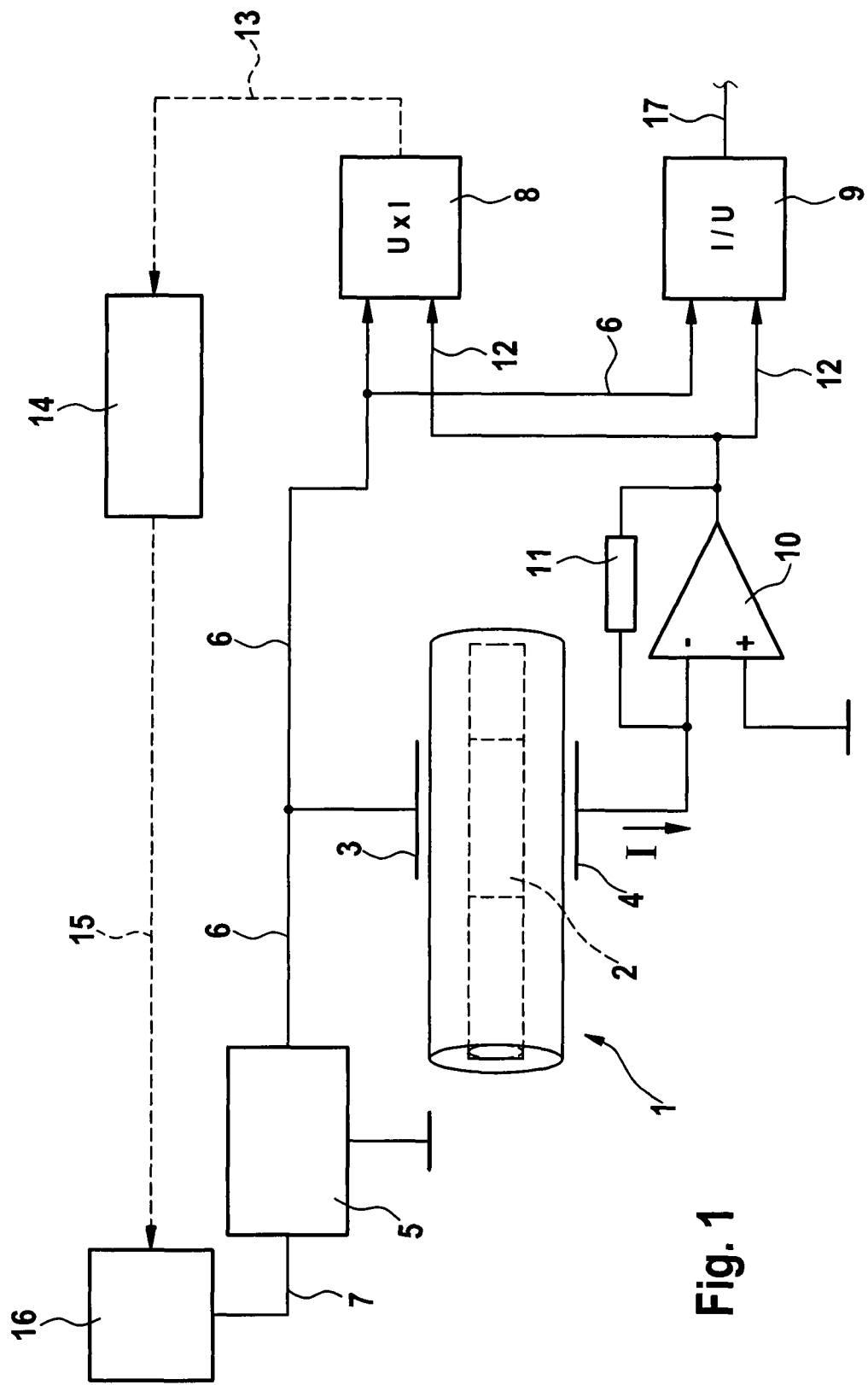
FIG. 1 shows a first embodiment of the invention, whereby the voltage is controlled such that the power dissipation is kept at a predefined value.

The voltage control circuitry for the detection cell 1 further comprises an operational amplifier 10. The inverting input (−) of the operational amplifier 10 is connected with the receiver electrode 4, and the non-inverting input (+) is connected with ground. The resistor 11 couples the output of the operational amplifier 10 with the non-inverting input (−). The operational amplifier 10 and the resistor 11 act as an I/U converter: the AC current I flowing through the detection cell is converted into a proportional AC voltage signal 12, which is provided at the operational amplifier's output. The AC voltage signal 12 represents the AC current I passing though the detection cell. The AC voltage signal 12 is forwarded, as a second input, to the multiplier unit 8 and to the divider unit 9.

In the multiplier unit 8, the product of the HF voltage 6 and the AC voltage signal 12 is determined. The product U×I indicates the actual power dissipation within the detection cell volume 2. Preferably, a phase-sensitive evaluation of the product U×I is carried out, whereby the real part of the product U×I corresponds to the Joule heating within the detection cell volume 2, whereas the imaginary part does not contribute to the heat dissipation. The power feedback signal 13, which indicates the effective power dissipation in the detection cell volume 2, is forwarded to a control unit 14. There, the power feedback signal 13 is compared with a set value indicating the desired power dissipation. In dependence on the deviation between the actual power dissipation and the set value, a digital control signal 15 is generated. The digital control signal 15 is forwarded to the digital/analogue converter 16. There, it is converted into the DC control voltage 7, which in turn controls the magnitude of the HF voltage 6. Thus, a closed-loop control is established.

If the control unit 14 determines that the power feedback signal 13 is smaller than the set value, the digital control signal 15 will be changed such that the HF voltage 6 is increased. As a consequence, the power dissipation within the detection cell volume 2 will be increased as well. If the power feedback signal 13 is above the set value, the control unit 14 will modify the digital control signal 15 such that the HF voltage 6 and the power dissipation are decreased. For example, if a high conductivity sample band enters the detection cell volume 2, the control unit 14 will reduce the HF voltage 6 until the power dissipation is brought back to its desired value. By controlling the power dissipation, temperature bumps introduced by a change of the sample's conductivity are avoided. The control unit 14 is operated at a rate that allows to quickly react to any changes of the sample's conductivity.

The divider unit 9 is adapted for determining the quotient I/U, and as a result signal 17, the sample's conductivity is obtained. Preferably, the divider unit 9 is adapted for performing a phase-sensitive evaluation of the quotient I/U, and for separately determining the real part and the imaginary part of the sample's conductivity. Instead of the conductivity, another electrical property, like e.g. impedance, resistance, reactance, relative permittivity, and dielectric dispersion might be derived from the HF voltage 6 and the AC voltage signal 12.

Figure 2:
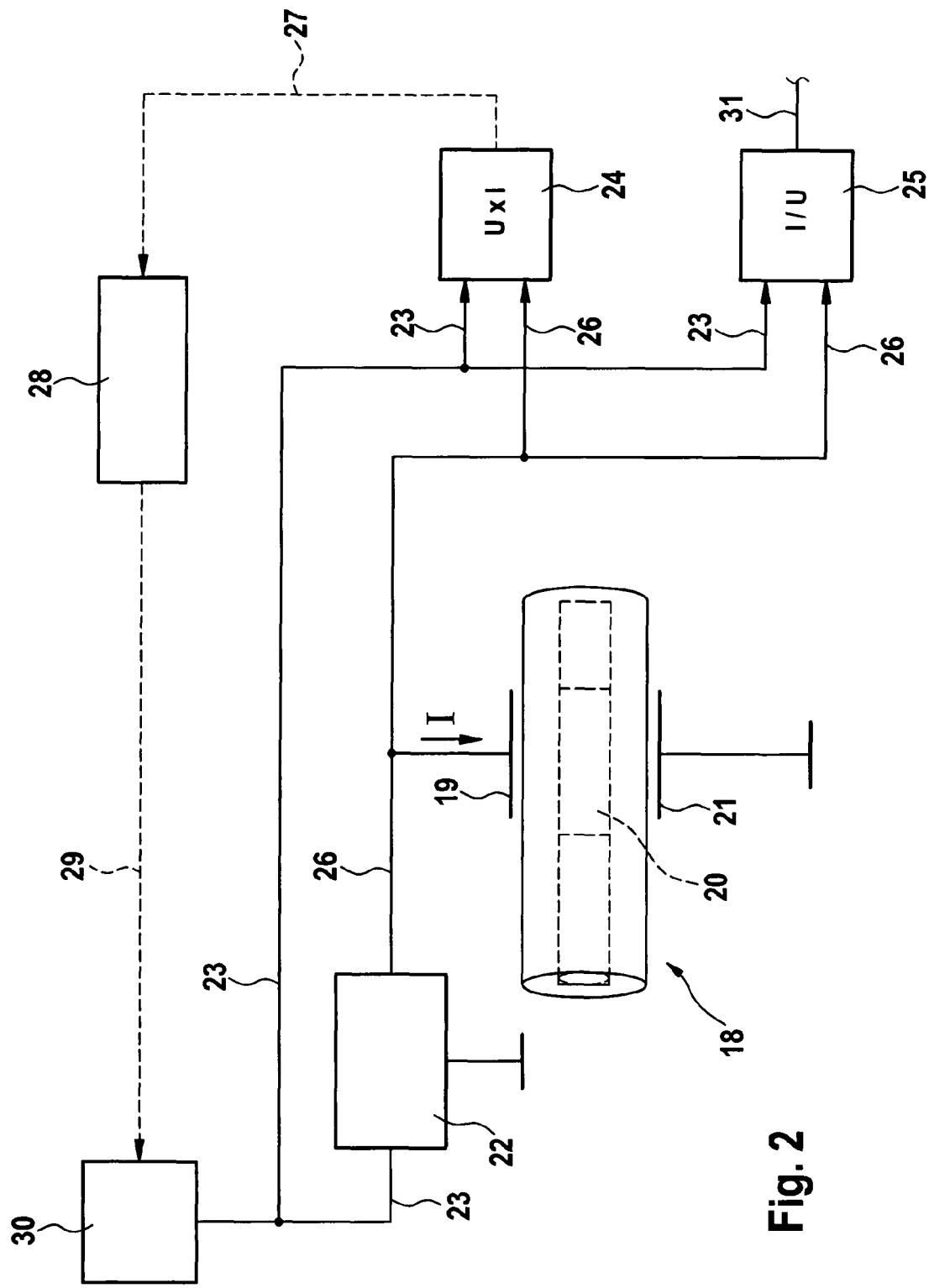
FIG. 2 shows a second embodiment of the invention, whereby the current is regulated such that the power dissipation is kept at a predefined value.

In FIG. 2, an alternative embodiment of the invention is shown. The detection cell 18 comprises a transmitter electrode 19 adapted for coupling an AC current to a detection cell volume 20, and a receiver electrode 21. The transmitter electrode 19 is connected to the output of the HF power supply 22, and the receiver electrode 21 is connected to ground. Instead of regulating the voltage, the HF power supply 22 is adapted for regulating the AC current I provided to the transmitter electrode 19. The AC current I is varied in dependence on the magnitude of the DC control voltage 23. The current control circuitry shown in FIG. 2 further comprises a multiplier unit 24, which determines the power dissipation U×I within the detection cell volume 20. The DC control voltage 23, which represents the magnitude of the AC current I, is provided, as a first input, to the multiplier 24 and to a divider 25. The power supply's output signal 26 is provided, as a second input, to the multiplier 24 and to the divider 25. By multiplying the DC control voltage 23, which represents the AC current, with the power supply's output signal 26, the power dissipated in the detection cell volume 20 is obtained. The power feedback signal 27 provided by the multiplier 24 is forwarded to the control unit 28, and there, the actual power dissipation is compared with a desired power dissipation. The control unit 28 is adapted for providing a digital control signal 29 to the digital/analogue converter 30, which converts the digital control signal 29 into the DC control voltage 23. If the power feedback signal 27 is below the desired power dissipation, the control unit 28 will modify the digital control signal 29 in a way that the AC current I is increased. In contrast, if the power feedback signal 27 is above the desired power dissipation, the control unit 28 will modify the digital control signal 29 in a way that the AC current I is reduced.

The divider unit 25 is adapted for receiving the DC control voltage 23, which indicates the magnitude of the AC current I, and the power supply's output signal 26, which is the AC voltage across the detection cell. The divider unit 25 is adapted for determining the quotient I/U, and for generating a signal 31 indicating the sample's conductivity. Preferably, a phase-sensitive evaluation of the sample's conductivity is performed.

The invention claimed is:

1. Control circuitry configured for determining an electrical property of a sample in a detection cell volume of a detection cell, in order to detect and characterize a compound in the sample, the control circuitry comprising:
    a power supply configured for providing at least one of a voltage and a current to the detection cell;
    a power evaluation unit configured for determining an actual power dissipation in the detection cell volume based on a product of a current passing through the detection cell volume and one of the voltage provided by the power supply or a control voltage, wherein the detection cell volume is part of a detection flow path, with a fluid sample passing through the detection cell volume;
a control unit configured for comparing the actual power dissipation with a desired power dissipation, and for regulating at least one of the voltage and the current provided by the power supply to drive the actual power dissipation towards the desired power dissipation; and
a divider unit configured for determining a quotient of the current passing through the detection cell volume and one of the voltage provided by the power supply or the control voltage, for deriving the electrical property of the sample.

2. The control circuitry of claim 1, wherein the control unit is configured for determining a deviation between the actual power dissipation and the desired power dissipation, and for regulating the power supply's voltage in a way that said deviation is minimized.

3. The control circuitry of claim 1, wherein the detection cell is configured for detecting at least one of an electrical property of a fluid sample and compounds of a fluid sample that have been separated in a preceding separation flow path.

4. The control circuitry of claim 1, wherein the power supply is configured for providing at least one of an AC voltage and an AC current to the detection cell.

5. The control circuitry of claim 1, wherein the electrical property is at least one of: conductivity, complex conductivity, impedance, resistance, reactance, relative permittivity, dielectric dispersion.

6. The control circuitry of claim 1, further comprising at least one of the following features:
the control unit is configured for providing a voltage control signal to the power supply;
the power supply is a voltage controlled power supply, with the voltage provided by the power supply being varied in accordance with the voltage control signal;
in case the actual power dissipation is smaller than the desired power dissipation, the control unit is configured for modifying the voltage control signal in a way that the power supply's voltage is increased, and wherein in case the actual power dissipation is higher than the desired power dissipation, the control unit is configured for modifying the voltage control signal in a way that the power supply's voltage is decreased.

7. The control circuitry of claim 1, wherein the control unit is operated at a rate between 100 Hz and 100 kHz.

8. The control circuitry of claim 1, wherein the divider unit is configured for performing a phase-sensitive evaluation of the quotient of the current and the voltage.

9. The control circuitry of claim 1, further comprising at least one of the following features:
the detection cell is a contactless conductivity detection cell; and
the power evaluation unit comprises a multiplier unit.

10. The control circuitry of claim 1, further comprising:
a current determination unit configured for determining the current passing through the detection cell volume,
wherein the current determination unit comprises an operational amplifier having a first input for receiving the current passing through the detection cell volume, a second input connected to ground, and an output connected to an input of the divider unit.

11. A system for determining an electrical property of a fluid sample, the system comprising:
a detection cell defining a detection cell volume, wherein the detection cell volume is part of a detection flow path, with the fluid sample passing through the detection cell volume, the detection cell comprising:
a transmitter electrode configured for coupling a current to the detection cell volume; and
a receiver electrode configured for receiving the current that has been coupled to the detection cell volume;
a power supply configured for providing the current or the current and a voltage to the detection cell;
a current determination unit configured for determining the current coupled to the detection cell volume;
a power evaluation unit configured for determining an actual power dissipation in the detection cell volume based on a product of the current determined by the current determination unit and one of the voltage provided by the power supply and a control voltage;
a control unit configured for comparing the actual power dissipation with a desired power dissipation, and for regulating at least one of the voltage and the current of the power supply in a way that the actual power dissipation is driven towards the desired power dissipation; and
a divider unit configured for determining a quotient of the current determined by the current determination unit and one of the voltage provided by the power supply or the control voltage, for deriving the electrical property of the fluid sample.

12. The control circuitry of claim 11, wherein the power evaluation unit comprises a multiplier unit for determining the actual power dissipation as the product of the voltage and the current.

13. The control circuitry of claim 12, wherein the multiplier unit is configured for performing a phase-sensitive evaluation of the product of the voltage and the current.

14. The system of claim 11, wherein the transmitter electrode and the receiver electrode are not in direct contact with the fluid sample.

15. The system of claim 11, wherein the transmitter electrode is configured for capacitively coupling a current to the detection cell volume, and wherein the receiver electrode is configured for capacitively receiving the current that has been coupled to the detection cell volume.

16. The system of claim 11, further comprising at least one of the following features:
the transmitter electrode and the receiver electrode are arranged in a radial geometry;
the transmitter electrode and the receiver electrode are arranged in an axial geometry;
the detection cell is implemented as a part of a microfluidic chip device.

17. The system of claim 11, wherein the current determination unit comprises:
an operational amplifier having a first input connected to the receiver electrode for receiving the current and a second input connected to a reference voltage; and
a resistor connected between the first input and an output of the amplifier.

18. A separation system comprising:
a separation flow path configured for separating sample compounds of a given sample;
control circuitry configured for determining an electrical property of the sample, the control circuitry comprising:
a detection cell defining a detection cell volume, wherein the detection cell volume is part of a detection flow path, with the sample passing through the detection cell volume, the detection cell comprising:
a transmitter electrode configured for coupling a current to the detection cell volume; and a receiver electrode configured for receiving the current that has been coupled to the detection cell volume;

a power supply configured for providing the current or the current and a voltage to the detection cell;

a current determination unit configured for determining the current coupled to the detection cell volume;

a power evaluation unit configured for determining an actual power dissipation in the detection cell volume based on a product of the current determined by the current determination unit and one of the voltage provided by the power supply and a control voltage;

a control unit configured for comparing the actual power dissipation with a desired power dissipation, and for regulating at least one of the voltage and the current of the power supply so that the actual power dissipation is driven towards the desired power dissipation; and a divider unit configured for determining a quotient of the current determined by the current determination unit and one of the voltage provided by the power supply or the control voltage, for deriving the electrical property of the sample, wherein the electrical property is used to detect and characterize a compound in the sample.

19. The separation system according to claim 18, wherein the sample comprises a fluid sample.

20. The separation system of claim 18, comprising at least one of: an electrophoresis system, a liquid chromatography system, an electro-chromatography system, and an isotachophoresis system.

21. The system of claim 17, wherein the first input comprises an inverting input and the second input comprises a non-inverting input, and the reference voltage comprises ground.

* * * * *